Figure 1B:
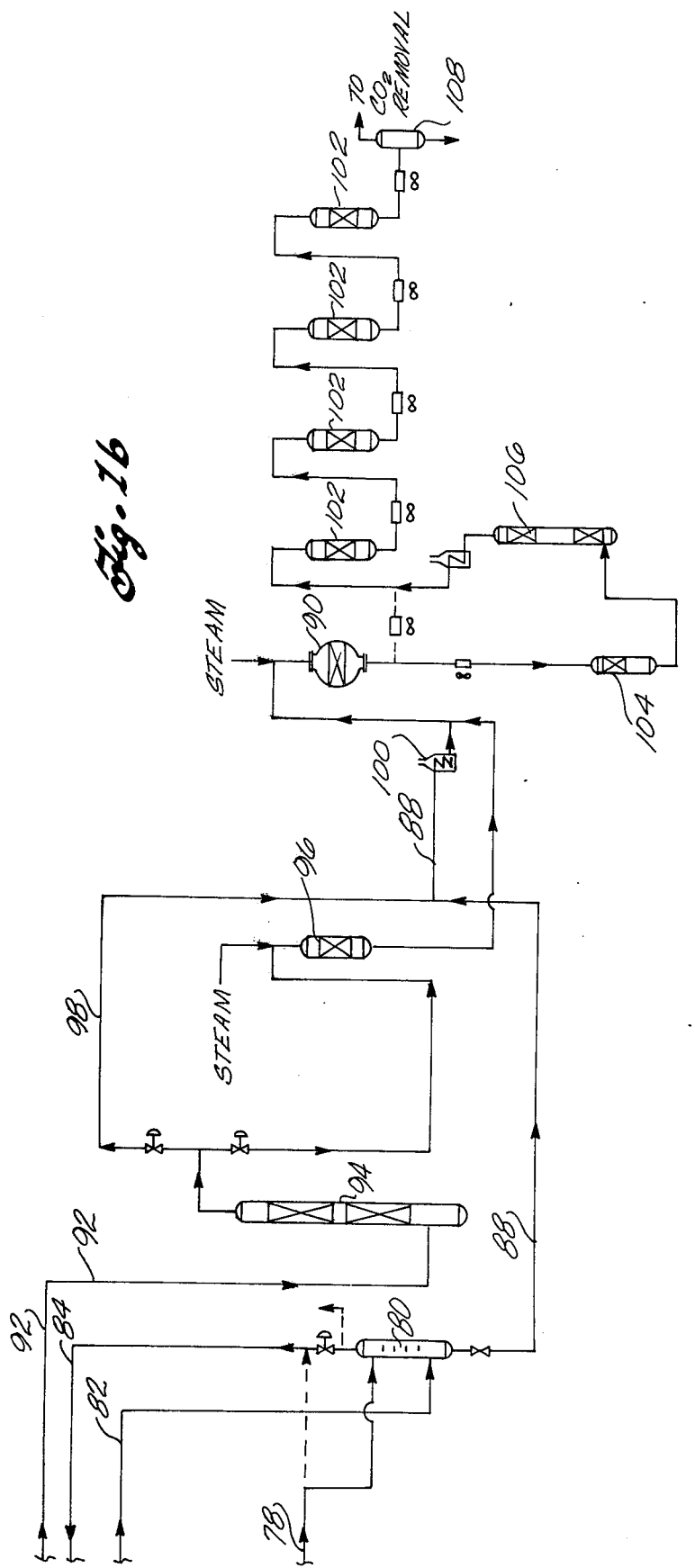

United States Patent [19]

McNamee et al.

[11] 4,115,075
[45] * Sep. 19, 1978

[54] PROCESS FOR THE PRODUCTION OF FUEL VALUES FROM CARBONACEOUS MATERIALS

[75] Inventors: Gerald P. McNamee, Santa Ana; Theodore R. Roszkowski, Malibu; David W. Stanbridge, Pacific Palisades; Gerald A. White, Los Angeles, all of Calif.

[73] Assignee: The Ralph M. Parsons Company, Pasedena, Calif.

[*] Notice: The portion of the term of this patent subsequent to Sep. 27, 1994, has been disclaimed.

[21] Appl. No.: 779,922

[22] Filed: Mar. 21, 1977

Related U.S. Application Data

[63] Continuation-in-part of Ser. No. 707,004, Jul. 20, 1976, Pat. No. 4,050,908.

[51] Int. Cl.² .................... C10J 3/16; C10K 3/04
[52] U.S. Cl. .................... 48/197 R; 48/210; 48/214 A; 208/8; 260/449.6 M
[58] Field of Search ....... 208/8; 260/449 M, 449.6 M; 48/197 R, 206, 210, 214 A

[56] References Cited

U.S. PATENT DOCUMENTS

| 3,598,718 | 8/1971 | Gleim et al. | 208/8 |
| 3,726,784 | 4/1973 | Correa et al. | 208/8 |
| 3,755,136 | 8/1973 | Fields et al. | 208/8 |
| 3,938,968 | 2/1976 | White et al. | 48/197 R |

Primary Examiner—S. Leon Bashore
Assistant Examiner—Peter F. Kratz
Attorney, Agent, or Firm—Christie, Parker & Hale

[57] ABSTRACT

A slurry of particulate carbonaceous material such as coal and a liquid hydrocarbon solvent formed from liquefaction of the carbonaceous material in the presence of hydrogen are combined with hydrogen in a liquefaction zone operated at temperatures from 700° to 1000° F, and pressures up to about 2500 psi. There is generated vapor and liquid hydrocarbons and solid residue. Light liquid hydrocarbons may be recovered as a product or ultimately converted to methane. Another portion of the liquid is recycled as the hydrocarbon solvent. The higher boiling liquid hydrocarbons and the solid residue are subjected to gasification to yield a synthesis gas which serves as a stripping gas stream used for separating the products of liquefaction into useful constituents. Preferably, all of the synthesis gas formed in the process, hydrocarbon vapor, and the light liquid hydrocarbons are converted by a combination of reforming and methanation operations to methane.

42 Claims, 2 Drawing Figures

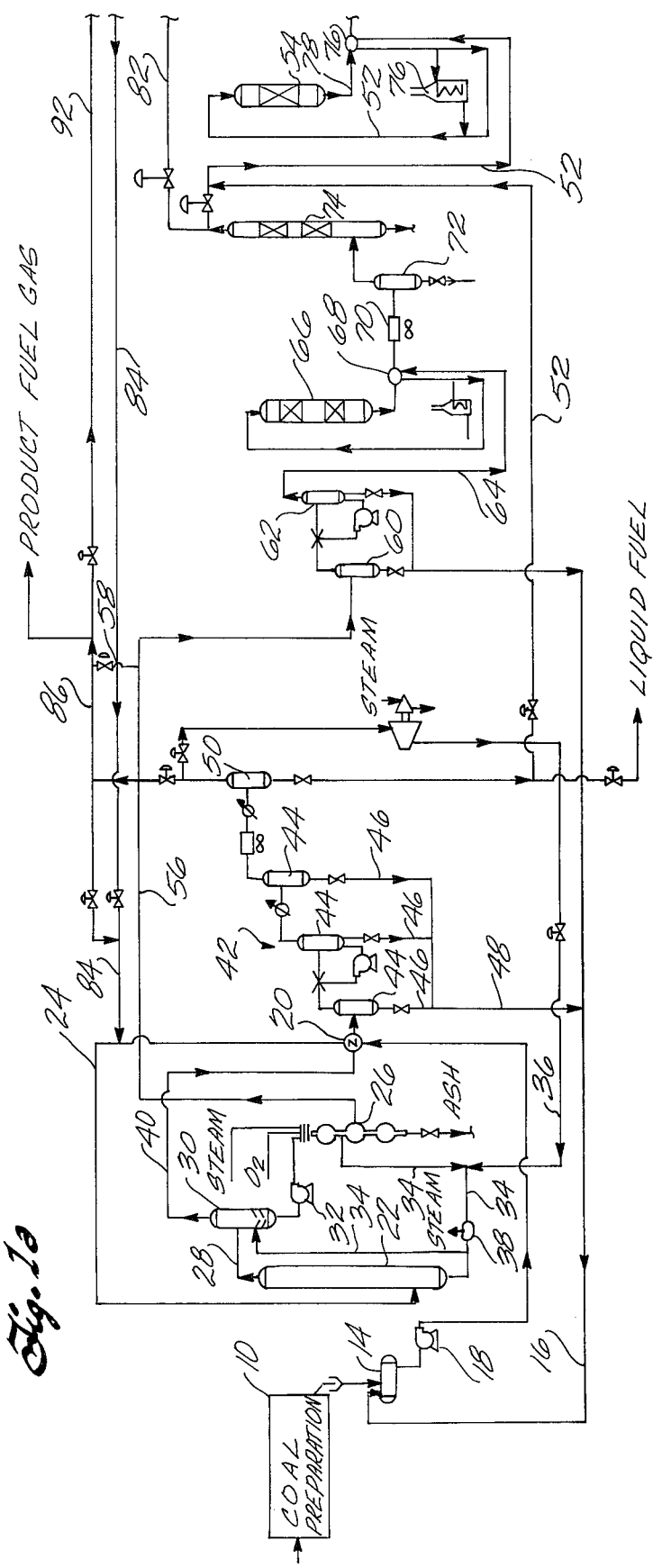

PROCESS FOR THE PRODUCTION OF FUEL VALUES FROM CARBONACEOUS MATERIALS

CROSS REFERENCE TO RELATED APPLICATIONS

This is a continuation-in-part of our Application Ser. No. 707,004 filed July 20, 1976 now U.S. Pat. No. 4,050,908.

BACKGROUND OF THE INVENTION

Dwindling reserves of liquid fossil fuels have placed greater emphasis on solid carbonaceous materials, especially coal, as a source of energy. An energy source of particular concern is methane, as it is highly desired to convert the available liquid fossil fuels to other products. Attention, therefore, has been strongly focused on processes which are directed to the ultimate conversion of coal into methane.

A need exists for a highly efficient process for the production of methane from coal and one which is sufficiently flexible to provide alternate liquid and gaseous fuel products.

SUMMARY OF THE INVENTION

According to the present invention, there is provided a process for the production of a fuel gas and a liquid fuel from coal, both of which may be ultimately converted to methane.

An operation basic to the instant invention is the formation of a reformable liquid hydrocarbon and a vapor stream comprising hydrocarbons, carbon monoxide, and carbon dioxide, and hydrogen from a carbonaceous material such as coal. The vapor stream is subjected to a methanation operation in the presence of a high temperature methane forming alumina based catalyst, as defined below, in a first methanation zone. The effluent is combined with the liquid hydrocarbon in a catalytic reforming stage, where at a temperature from about 1200° to about 1500° F., the hydrocarbons are reformed to yield an effluent gas comprising steam, hydrogen, carbon monoxide, carbon dioxide and methane. The effluent gas stream thus formed is passed to at least one additional methanation stage where hydrogen and carbon monoxide react to form methane in the presence of a high temperature methane forming alumina based catalyst under conditions described below.

The preferred overall operation of the present invention involves reacting a slurry of a particulate carbonaceous material in a liquid hydrocarbon solvent predominantly composed of hydrocarbons boiling up to about 750° F., preferably from about 300° to about 750° F., and more preferably from about 500° to about 750° F., and generated as a consequence of liquefying coal in the presence of hydrogen, solvent with a hydrogen containing gas in a liquefaction zone maintained at a temperature from about 700° to about 1000° F., preferably from about 800° to about 900° F., and at a pressure up to about 2500 psi, preferably 1000 to 1500 psi depending upon the effective partial pressure of the hydrogen containing gas. The carbonaceous material may be added to the liquefaction zone or as a slurry in the liquid hydrocarbon solvent. Residence time in the liquefaction zone is sufficient to convert at least a substantial portion of the carbonaceous material to hydrocarbons which are fluid at the operating temperature and pressure of the liquefaction zone. The products include hydrocarbon vapors, liquid hydrocarbons, and a solid residue of liquefaction.

The effluent from the liquefaction zone is combined with a synthesis gas in a stripping zone. There, the synthesis gas serves to form a vapor fraction comprising hydrocarbons, carbon monoxide, carbon dioxide and hydrogen, and leaves a liquid-solids fraction composed of heavy hydrocarbons boiling above the temperature at which the separation occurs and the solid residue of liquefaction.

The liquid-solids fraction from the stripping zone is combined with a source of combined oxygen such as steam and/or carbon dioxide and oxygen in an amount sufficient to gasify essentially all of the carbon contained in the fraction in a gasification zone to generate a synthesis gas comprising the oxides of carbon, hydrogen and methane to the extent present or formed. At least a major portion of the synthesis gas is passed to the stripping zone to achieve the separation between the vapor fraction and the liquid-solids fraction.

After being utilized for stripping, the synthesis gas may be recovered with vaporized hydrocarbons containing up to about 5 hydrocarbon atoms as a product fuel gas and/or a portion utilized for its hydrogen content in the liquefaction zone. When recovered, the synthesis gas, with the vaporized hydrocarbon, may be reformed to additional synthesis gas and methane.

Of the vaporized hydrocarbons from the stripping zone a fraction may be separated as a light liquid hydrocarbon fuel containing more than 5 carbon atoms and boiling up to 500° F., preferably up to 300° F., and the balance recycled as the hydrocarbon solvent for coal. A product fuel gas and product liquid fuel if recovered, would contain hydrogen sulfide and the product streams would be ultimately treated for its removal.

The process preferably is utilized for production of methane. For its production, a minor portion of the synthesis gas may be converted into a hydrogen rich gas stream for feed to the liquefaction zone and to hydrotreat the light liquid hydrocarbon fraction to eliminate bound sulfur. The pressurized light liquid hydrocarbon is passed to a reforming zone along with a portion of the residual vapor fraction formed as a consequence of the recovery of the light liquid hydrocarbon fraction, which residual vapor fraction may be previously stripped of at least a portion of contained carbon dioxide and hydrogen sulfide. The unit processes of this invention insofar as the methanation and reforming operations are concerned, are not dependent upon sulfur removal. The sulfur may be left in the various streams or removed as desired and hydrotreating avoided.

The balance of the vapor fraction which may be carbon dioxide and hydrogen sulfide lean may be passed to the methanation zone containing a high temperature methane forming alumina based catalyst. Such a catalyst contains from about 5 to about 50% by weight, preferably about 5 to about 35% by weight of at least one metal of the third period of Group VIII of the Periodic Table on a temperature stable alumina support. The methanation zone is maintained at a temperature suited for initiation of methanation for the catalyst employed and has an inlet temperature of from about 800° to about 900° F. or less and an outlet temperature up to about 1500° F. Methane is produced in the presence of steam with generation of exothermic heat. The effluent of the methanation zone is fed to the reforming zone to supply the heat requirements of the endothermic reforming reaction. The temperature stable aluminas which may be employed are a ceramic alumina, gamma alumina, delta alumina, theta alumina or their mixtures.

The gaseous product resulting from the reforming of the light hydrocarbons and the carbon oxides are passed to at least one additional methanation stage where hydrogen and carbon monoxide react to form additional methane. Preferably, a plurality of methanation stages are employed, each operating under the conditions similar to the first methanation stage with intermediate removal of heat between each stage.

In a preferred operation, the gas stream after reforming is subject to a stage of catalytic hydrolysis where any residual organic sulfides are decomposed and converted to hydrogen sulfide which is subsequently removed from the gas stream before passage to the further methanation stage or stages.

In employing the process as described, generally about 60 to 80% of the carbon in the coal, exclusive of the carbon present in the hydrocarbon solvent, appears in the feed to be gasified, about 10 to 20% as the light liquid hydrocarbon, and about 10 to 30% as vaporized hydrocarbons.

THE DRAWINGS

FIGS. 1a and 1b schematically illustrate the process of this invention.

DESCRIPTION

With reference to the Drawings, normally a solid carbonaceous material such as coal, shale oil, petroleum tars, tar sands and the like is prepared by crushing or grinding operations in preparation unit 10. The preferred carbonaceous material is coal which may be anthracite coal, bituminous coal, sub-bituminous coal, peat, lignite and the like. Typically, the solid carbonaceous material is ground to a particle size less than about 40 mesh, with a major portion, e.g., about 80% of the particles, being less than about 200 mesh. The particles after comminution may be dried to about a 2% moisture content. The comminuted particles may be dry fed to liquefaction zone 22 or blended in slurry tank 14 with a liquid hydrocarbon solvent, supplied to slurry tank 14 by line 16 and/or a reservoir (not shown). The liquid hydrocarbon solvent comprises hydrocarbons having boiling points below about 750° F. and generated by liquefaction of the solid carbonaceous material in the presence of hydrogen. The preferred liquid hydrocarbon solvent is one comprising hydrocarbons boiling in the range from about 300° to about 750° F., and more preferably in the range from about 500° to about 750° F.

The effluent from the slurry tank 14, if used, is pressured and transferred by pump 18 through heat exchanger 20 in indirect exchange with the vapor effluent of stripper 30 and passed by line 24 to liquefaction zone 22 where liquefaction occurs in the presence of hydrogen. The source of hydrogen may be a portion of the fuel gas resulting from stripping of the effluent of the liquefaction zone with a synthesis gas or a hydrogen rich gas produced from a synthesis gas generated in the process.

Typically the weight ratio of hydrocarbon solvent to solid carbonaceous material is from about 1:1 to about 3:1 depending on the effectiveness of the liquid in absorbing the heat of liquefaction. The preferred range is from about 1.5:1 to about 2.5:1.

Liquefaction zone or dissolver 22 is operated at an elevated temperature normally in the range from about 700° to about 1000° F., preferably from about 800° to about 900° F., and a high pressure, typically up to about 2500 psi and preferably from about 1000 to about 1500 psi.

The amount of hydrogen consumed by reaction in dissolver 22 is normally about 2% by weight of the solid carbonaceous material, e.g., about 2 pounds of hydrogen per 100 pounds of coal. Excess hydrogen may be provided to maintain a desired partial pressure of hydrogen in dissolver 22 as well as for control of temperature.

In dissolver 22, the solid carbonaceous material in the presence of the liquid hydrocarbon solvent and hydrogen undergoes thermal reactions with accompanying hydrogenation of the product and hydrocracking to yield hydrocarbons having a broad boiling point distribution. The liquid hydrocarbon solvent also serves as a sink to control reaction temperature.

The effluent of dissolver 22 in line 28 is a three phase mixture which includes unutilized constituents of the source of hydrogen, hydrocarbon vapors generated through liquefaction, hydrocarbons which are liquid at the operating conditions in dissolver 22 and a solid residue of liquefaction. The mixture passes to stripper 30 operated at essentially the same pressure as dissolver 22. In stripper 30 the dissolver effluent is combined with a gas comprising a major portion if not all of the synthesis gas generated in gasifier 26 from a portion of the products of liquefaction. Normally from about 60 to 100%, more typically from about 80 to about 90%, of the generated synthesis gas serves as stripping gas. The synthesis gas in line 34 may or may not be cooled in steam generator 38 as determined by temperature requirements set by the feed to stripping zone 30. If desired a portion of compressed vapor products from separator 50 may be used to quench the syngas ahead of steam generator 38.

The steam generated as a consequence of cooling of the synthesis gas is at approximately 1500 psi and is used in the process, for example, for driving compressors, or for reforming and methanation. Ash is withdrawn from the base of gasifier 26.

Stripper 30 yields a vapor and a liquid solids stream. Besides the oxides of carbon and hydrogen contained in the stripping gas, the vapor stream comprises hydrocarbons boiling below the normal operating temperature and pressure of stripping zone 30. Typically, hydrocarbons boiling above 750° F. are separated in admixture with the solid residue of liquefaction. The lower boiling hydrocarbons remain in the vapor although, as will be understood, an overlap of materials from each fraction formed will appear in the other fraction.

The mixture of liquids and solids is transferred by pump 32 to gasifier 26 where through the addition of oxygen and a source of combined oxygen, the carbon present in both the liquids and solids is converted in bulk to a syngas comprising hydrogen and the oxides of carbon with some methane at temperatures from about 2200° to about 2600° F. at pressures from about 1200 to about 2500 psig. By a "source of combined oxygen", there is meant a compound which will yield oxygen for reaction at the temperatures employed. The preferred source of combined oxygen is steam and/or carbon dioxide.

At least the bulk of the syngas generated is preferably passed by line 34 for combination with cooled compressed gas in line 36 and typically quenched to a temperature of about 1700° F. and cooled in steam generator 38 to from about 700° to about 1000° F. for feed to stripper 30. The balance of the syngas is either blended with side stream 58 as part of product fuel gas or converted to hydrogen rich gas for feed to dissolver 22.

The vapor stream from stripper 30 may be passed directly to reformer 90 where the hydrocarbons, heavier then methane and boiling up to approximately 750° F., are converted to syngas and additional methane through reaction with steam in the presence or absence of sulfur, and preferably as shown, is passed by line 40 after partial cooling in heat exchanger 20 to a first liquid recovery system 42.

There, when desired, through a plurality of separators 44 operating in connection wherein with sundry cooling and scrubbing operations, gaseous feed is reduced to a temperature consonant for recovery of the liquid hydrocarbon solvent. Separated with the liquid hydrocarbon solvent having a boiling point up to 750° F., preferably from about 300° to about 750° F., and preferably from about 500° to 750° F., are residual carryover solids from the stripper 30. The condensate from each separator 44 employed is passed by line 46 for combination in line 48. The combined liquid hydrocarbon solvent and collected solids are passed by line 16 to slurry mixer 14 or solvent storage (not shown).

The vapor effluent after first cooling to approximately 150° F. is passed to light liquid hydrocarbon separator 50. The light liquid hydrocarbon condensate formed contains, with some overlap, $C_5$ hydrocarbons up to the boiling point of the hydrocarbons recovered in separator system 42, e.g., up to about 800° F., preferably up to about 500° F., more preferably up to 300° F. The light liquid hydrocarbon from separator 50 may be recovered as liquid fuel or transferred by line 52 with combined hydrogen rich gas formed from a minor portion of the syngas from gasifier 26 to hydrotreater 54.

As indicated, a hydrogen rich gas may be formed from a portion of the gasifier effluent in line 56, which contains from about 5 to 50% hydrogen, to the extent gasifier product is not withdrawn by line 58 as product fuel gas. The syngas in line 56 is passed to separator 60 and then to separator 62 through a venturi scrubber where any solids and any unconverted hydrocarbons present are removed from the gas stream and returned to line 16 for recycling to mixer 14. The effluent from separator 62 is passed by line 64 to heat exchanger 68 where the gas is raised to a temperature at which it will undergo a catalytic water gas shift and to shift converter 66 where the hydrogen content of the reactants is increased. The effluent from shift converter 66 after being cooled in exchanger 68 and air cooler 70 may be passed through separator 72 and through absorber 74 where it is stripped of at least a portion of the contained carbon dioxide and hydrogen sulfide in a manner well known in the art.

Independent of whether the absorber is used, the hydrogen rich gas may be split. A portion may be combined with the light liquid hydrocarbon in line 52 and passed from line 52 after heat exchange with the effluent of hydrotreater 54 in exchanger 76 to hydrotreater 54. Fired heater 76 serves for start up and to the extent required as a supplemental heater.

Processing in hydrotreater 54, if employed, serves to release the bound sulfur from the light liquid hydrocarbon as hydrogen sulfide. Conversion normally occurs in the presence of a hydrotreating catalyst with the temperature and pressure being dictated by the severity of treatment required to cleave the carbon sulfur bonds.

The effluent from hydrotreater 54, if employed, is passed by line 78 to hydrogen sulfide stripper 80 where it is combined with the balance of the hydrogen rich gas in line 82 from carbon dioxide absorber 74. In hydrogen sulfide stripper 80 hydrogen rich gas carries off the released hydrogen sulfide. The hydrogen rich gas may be returned in line 84 as the source of hydrogen to line 24 for feed to dissolver 22. In the alternative or in combination, a portion of the vapor effluent of light liquid hydrocarbon separator 50 may be provided by line 86 as the source of hydrogen in dissolver 22. Another alternative is simply to purge the hydrogen sulfide-hydrogen mixture from stripper 80.

The treated light hydrocarbon oil still containing or substantially free of hydrogen sulfide may be passed by line 88 for combination with a part of a purified vapor stream from separator 50 and passed to reformer 90. For purification, the vapor effluent from separator 50 is passed by line 92 to acid gas scrubber 94 for removal of, as desired, hydrogen sulfide and carbon dioxide.

The effluent from absorber 94 when employed is split. A portion is passed to a first methanator in stage 96 which is operated at an inlet temperature above about 800° to 900° F. with an outlet temperature of up to about 1500° F., and employs a high temperature methane forming alumina based catalyst.

By a "high temperature methane forming alumina based catalyst" there is meant a catalyst containing from about 5 to about 50 percent by weight, preferably from about 5 to about 35 percent by weight of a metal from the Third Period of Group VIII of the Periodic Table with Atomic Weights as published in Perry's *Chemical Engineers Handbook,* Third Edition, McGraw Hill, 1950, i.e, nickel, cobalt and iron on an alumina support. Nickel and cobalt are the preferred metals with nickel particularly preferred.

One of the supports is a ceramic alumina which is rendered thermally stable by heat treating the support, as by calcining and the like, at temperatures above the temperature at which reaction is to occur prior to depositing the metal on the support. Such supports have a relatively low surface area, i.e. 10 $m^2/g$ or less, and the alumina content maximized to prevent other constituents, such as silica, from being volatilized and contaminating heat exchanger surfaces. Using a support of this nature, methanation will begin at a temperature of about 900° F. and can be allowed to proceed until temperatures of about 1600° F. are realized.

Other preferred supports are prepared from a selected pure alumina made from a finely crystallized alumina monohydrate, such as boehmite and ultrafine boehmite. In their preparation, it is essential to use a pure, single phase alumina hydrate that is transformed successively into a gamma and/or a delta form following dehydration by calcining. The gamma form exists at temperatures up to about 800° C. and the delta form up to about 1050° C. At the temperature interface of about 800° C., a mixture of the two forms exist. The normally calcined alumina which may be the gamma and/or delta form is mechanically and thermally stable up to approximately 1000° C. as demonstrated by retaining a surface area in the range of about 40 to about 160 $m^2/g$ or more, preferably from about 50 to about 160 $m^2/g$ or more. At temperatures about 1050° C., almost simultaneous transformation to the theta then alpha form occurs.

A stable theta form, with preserved mechanical properties and a surface area of 30 m²/g or more is provided by treating or modifying the pure boehmite alumina hydrate before or after dehydration with rare earth oxides, such as those whose cation have an Atomic Number between 59 and 72. The theta form so prepared is thermally and mechanically stable and will retain a surface area up to a temperature of approximately 1250° C. Modification of the precursor also aids in retention of surface area for the gamma and delta forms.

The support of these are described in greater detail in Chapter 12 of "Catalysts for the Control of Automobile Pollutants", James E. McEvoy, ACS Advances in Chemistry Series, Number 143.

Besides the support described in U.S. Pat. No. 3,938,968, the presently preferred catalyst supports are SCS 59 Spheralite, SCS 109 RT Spheralite, and G FS 300 extrudate supplied by Rodia, Inc., Monmouth Junction, N.J., Chemical Division of Rhone-Poulenc; SN 7085 and SN 7086, supplied by Catalyst and Chemicals, Inc., Lousiville, Ky., and Alumina Hydrate SA-Medium supplied by Kaiser Aluminum.

Using an alumina support of the invention, the catalyst is prepared by dipping the support into an aqueous solution of one or more soluble Group VIII metal salts normally containing 5 to 20 weight percent of the metal. The dipped particles are then calcined at temperatures in the range of 300° to 450° C. to convert the salt to the oxide. Prior to use, the oxide is reduced with hydrogen at a temperature up to 1200° F., while the catalyst provided contains a total of from about 5 to about 50% by weight, preferably 5 to about 35% by weight of the Group VIII metals based on the weight of the Group VIII metals and the support. Other metals may be present, including as modifying metals, the alkali metal oxides and carbonates, preferably potassium carbonate and potassium oxide. Other metals such as barium oxide, magnesium oxide, and the like may also be used.

The catalysts are functional in the presence of hydrogen sulfide. Actual feed temperature to a methanation zone in which they are employed is dependent on carbon monoxide content. As it is reduced, thus diminishing the potential of carbonyl formation, so can feed temperature lower the limit to the temperature at which carbonyl formation occurs.

The exotherm of the high temperature effluent of methanator 96 provides the heat to account for the endothermic reaction which occurs in reformer 90.

The balance of the effluent from absorber 94 which comprises hydrocarbons containing up to about 5 carbon atoms, hydrogen and carbon monoxide, is passed by line 98 to line 88 where it is combined with the light hydrocarbons and added after further heating in heater 100 to reformer 90. Reformer 90 operates at a temperature from 1200° to 1500° F., in the presence of steam employing a conventional reforming catalyst. Hydrocarbons introduced are reformed in the presence of steam at a temperature from 1200° to 1500° F. at system operating pressure to yield methane, hydrogen and the oxides of carbon. Operation in the desired temperature range is assured by the heat supplied from the effluent of the first adiabatic methanator 96.

After cooling the reformer effluent may be passed directly through a series of adiabatic bulk methanators 102 with cooling between each stage to increase the methane content of the gas stream to a desired level. Typically, the bulk methanators 102 are operated as described in U.S. Pat. No. 3,938,968, incorporated herein by reference, employing a high temperature methane forming alumina based catalyst as described above. For the gas compositions employed, inlet temperature may be reduced to 700° F. or less due to elimination of carbon monoxide by methane forming reactions in the previous methanation and reforming zones.

Preferably, the gas stream from reformer 90 is passed after cooling through hydrolysis convertor 104 containing a catalyst such as a cobalt molybdate catalyst or a hydrolysis catalyst where residual organic sulfur is converted to hydrogen sulfide which is removed in scrubber 106. While beneficial to the methanation operation as described in U.S. Pat. No. 3,938,968, this operation is essential where methanation occurs in a conventional manner as described, for instance, in U.S. Pat. No. 3,511,624 to Humphries et al, incorporated herein by reference. In conventional methanation, the catalysts employed are prone to poisoning by hydrogen sulfide. This is not true of the reforming and high temperature methane forming alumina based catalyst for the methanation system depicted. Such catalysts are sulfur tolerant, and the hydrogen sulfide can reduce steam requirements.

The final effluent of the bulk methanator, typically at a methane content of about 50%, may be passed after water removal in separator 108 to a $CO_2$ removal unit (not shown) to raise the methane content of the gas stream to the level desired for end use application. In addition, dry methanation may also be employed prior to or after CO removal, as described in U.S. Pat. No. 3,938,968.

EXAMPLE

Washed coal ground to a particle size less than 40 mesh is passed at a temperature of 100° F. to a slurry mixer and combined with a liquid hydrocarbon solvent at a temperature of 353° F., the weight ratio of liquid hydrocarbon solvent to coal being 2 pounds per pound. The resultant slurry at a temperature about 277° F. is pumped to a pressure of 1300 psig and preheated in indirect heat exchange with the vapor effluent of a stripper to 650° F. for feed to a liquefaction zone operating at a temperature between 820° F. and 870° F., and at a pressure of 1175 psig.

A hydrogen rich gas produced from an effluent of a gasification zone is combined with the slurry in a dissolver in an amount in excess of 2% by weight hydrogen based on the weight of coal. The effluent of the liquefaction zone containing vaporized hydrocarbons, liquid hydrocarbons, hydrogen, hydrogen sulfide and a solid residue is passed to a stripping zone operated at 1170 psig, along with a synthesis gas obtained from the gasification zone and entering at a temperature of 1100° F. and a pressure of 1175 psig.

The bottoms of the stripper at a temperature of 935° F. are passed to a gasification unit operated at 1255 psig where, upon the addition of oxygen and steam, the carbon is essentially completely gasified to carbon dioxide and carbon monoxide with attendant formation of hydrogen and some methane.

A major portion of the effluent of the gasification zone is passed to the stripper as stripper gas and the minor portion to production of hydrogen rich gas for the feed to the dissolver.

The vapor effluent of the stripping zone at 857° F. contains hydrogen, carbon monoxide, carbon dioxide, hydrogen sulfide and vaporized hydrocarbons. The effluent is first passed to a high pressure separator operated at 1155 psig at a temperature of 346° F., where there is collected a condensate of the liquid hydrocarbon solvent for recycle at a reduced pressure to a storage tank which feeds the slurry tank.

The gaseous effluent from the high pressure separator after cooling is passed to a gas-liquid separator operated at 1145 psig and 120° F. where there is formed a light liquid hydrocarbon and a vapor effluent containing hydrogen sulfide, carbon dioxide, carbon monoxide, hydrogen and vaporized hydrocarbons including $C_5$ and less hydrocarbons.

The light liquid hydrocarbon produced from the gas liquid separator is hydrotreated for release of bound sulfur and the hydrogen and contained hydrogen sulfide separated. The stripped and desulfurized liquid hydrocarbon is heated to 900° F. for passage to an adiabatic reformer operating at 1100° F.

Simultaneously, the vapor effluent from the liquid separator is treated for removal of hydrogen sulfide, carbonyl sulfide, ammonia and carbon dioxide and passed in part with steam after heating to 900° F. to a first methanation zone. The catalyst in the methanation zone is one consisting of 16% by weight nickel deposited on a high purity alumina support known as SAHT-99 manufactured and sold by the Carborundum Company. This support has a typical composition of 99.5% by weight $Al_2O_3$; 0.02% by weight $SiO_2$; 0.04% by weight $Fe_2O_3$ and 0.45% by weight $Na_2O$. The surface area is in a range of 0.5 to 5.5 $m^2$/gm.

The effluent of the methanator and another portion of the purified vapor are combined with the purified light liquid hydrocarbon in the adiabatic reformer. The effluent of the reformer after cooling to 700° F. is passed to a hydrolysis converter containing a cobalt molybdate catalyst. The effluent of the converter is cooled and passed to an acid gas removal unit for additional removal of $CO_2$, hydrogen sulfide and residual COS.

After reheating to 900° F., the gas stream is passed to four methanation zones in series with cooling between each stage of methanation to provide a feed temperature to each stage of 900° F. The catalyst employed in each methanation zone is the same as that employed in the first methanation zone.

After the last stage of methanation, the gas stream is cooled to first condense water and passed to a carbon dioxide separator.

After carbon dioxide separation, the gas stream is passed to a dry methanation stage containing a conventional methanation catalyst where methane content is increased. After final $CO_2$ removal and drying there is provided a substitute natural gas of higher than 90.0% methane content.

What is claimed is:

1. A process for the production of methane which comprises in combination the steps of:
   (a) reacting a slurry of a solid carbonaceous material in a liquid hydrocarbon solvent comprising hydrocarbons boiling up to about 750° F. and generated from the liquefaction of coal in the presence of hydrogen with a hydrogen containing gas in a liquefaction zone maintained at a temperature from about 700° to about 1000° F. and at a pressure up to about 2500 psi for a time sufficient to convert a substantial portion of the carbonaceous material to fluid hydrocarbons and a solid residue of liquefaction;
   (b) combining the effluent, fluid hydrocarbons and the solid residue of liquefaction from the liquefaction zone with a synthesis gas in a stripping zone and forming a liquid-solids fraction comprising liquid hydrocarbons boiling above the boiling point of the liquid hydrocarbon solvent and the solid residue of liquefaction and a vapor fraction comprising hydrocarbons, carbon monoxide, carbon dioxide and hydrogen;
   (c) combining, in a gasification zone, the liquid-solids fraction from the stripping zone with oxygen and a source of combined oxygen in an amount sufficient to gasify substantially all of the carbon contained in the liquid-solids fraction to generate a synthesis gas comprising hydrogen and the oxides of carbon;
   (d) passing a major portion of the synthesis gas to the stripping zone to form the vapor fraction;
   (e) separating the vapor fraction by cooling and condensation into a liquid hydrocarbon solvent fraction, a light liquid hydrocarbon fraction and a residual vapor fraction comprising hydrocarbons containing up to about 5 carbon atoms, carbon dioxide, carbon monoxide and hydrogen;
   (f) returning at least a portion of the liquid hydrocarbon solvent fraction to the liquefaction zone;
   (g) converting a minor portion of the synthesis gas from the gasification zone into a hydrogen rich gas stream;
   (h) passing at least a portion of the hydrogen rich gas stream as part of the hydrogen containing gas to the liquefaction zone;
   (i) methanating a portion of the residual vapor fraction in the presence of steam and a high temperature methane forming alumina based catalyst containing from about 5 to about 50% by weight of at least one metal of the third period of Group VIII of the Periodic Table on a temperature stable alumina support in a first methanation zone having an inlet temperature of at least about 800° F. and exit temperature up to about 1500° F.;
   (j) combining, with steam, the effluent of the methanation zone, the balance of the residual vapor fraction and the light liquid hydrocarbon in a catalytic reforming stage where, at a temperature from about 1200° to about 1500° F. maintained by the effluent of the methanation stage, hydrocarbons are reformed to yield an effluent gas stream comprising steam, hydrogen, carbon monoxide, carbon dioxide and methane; and
   (k) passing the effluent gas stream from the reforming stage to at least one additional methanation stage where the hydrogen and carbon monoxide react to form additional methane.

2. The process of claim 1 in which the effluent of the reforming stage, prior to passage to an additional methanation stage, is:
   (a) contacted in a hydrolysis zone with a catalyst to convert at least a portion of bound sulfur contained in the effluent of the reforming stage to hydrogen sulfide, and
   (b) treating the product of the hydrolysis zone to separate at least a portion of the formed hydrogen sulfide.

3. A process as claimed in claim 1 in which the alumina support is a temperature stabilized ceramic alumina heat treated to a temperature greater than the highest temperature in the methanation zone prior to the addition of the metal thereto.

4. A process as claimed in claim 1 in which the alumina support has a surface area of at least 30 $m^2$/g and selected from the group consisting of gamma alumina, delta alumina, theta alumina, and mixtures thereof.

5. A process as claimed in claim 3 in which the support is modified with a potassium compound selected from the group consisting of potassium oxide, potassium carbonate, and mixtures thereof.

6. A process as claimed in claim 4 in which the alumina is modified with rare earth oxides.

7. A process as claimed in claim 4 in which the support is modified with a potassium compound selected from the group consisting of potassium oxide, potassium carbonate, and mixtures thereof.

8. The process of claim 1 in which the liquid hydrocarbon solvent predominantly comprises hydrocarbons boiling in the range from about 300° to about 750° F.

9. The process of claim 1 in which the liquid hydrocarbon solvent predominantly comprises hydrocarbons boiling in the range from about 500° to about 750° F.

10. The process of claim 8 in which the light liquid hydrocarbon predominantly comprises hydrocarbons containing more than about 5 carbon atoms to hydrocarbons boiling up to about 300° F.

11. The process of claim 9 in which the light liquid hydrocarbon predominantly comprises hydrocarbons containing more than about 5 carbon atoms to hydrocarbons boiling up to about 500° F.

12. The process of claim 1 in which liquefaction occurs at a temperature from about 800° to about 900° F.

13. The process of claim 12 in which liquefaction occurs at a pressure from about 1000 to about 1500 psig.

14. The process of claim 1 in which from about 60 to about 90% of the synthesis gas is passed to the stripping zone.

15. The process of claim 1 in which from about 80 to about 90% of the synthesis gas is passed to the stripping zone.

16. The process of claim 2 in which the hydrogen rich gas is supplied to the liquefaction zone in a quantity to provide at least about 2% by weight of the weight of the solid carbonaceous material fed to the liquefaction zone.

17. The process of claim 1 in which the effluent gas from the reforming stage is at least passed through a plurality of methanation stages in series with cooling between each stage, each stage containing a high temperature methane forming alumina based catalyst containing from about 5 to about 50% of at least one metal of the third period of Group VIII of the Periodic Table on a temperature stable alumina support, each methanation stage having an inlet temperature of at least about 700° F. and an outlet temperature up to about 1500° F.

18. The process of claim 2 in which the effluent gas from the reforming stage is at least passed through a plurality of methanation stages in series with cooling between each stage, each stage containing a high temperature methane forming alumina based catalyst containing from about 5 to about 50% of at least one metal of the third period of Group VIII of the Periodic Table on a temperature stable alumina support, each methanation stage having an inlet temperature of at least about 700° F. and an outlet temperature up to about 1500° F.

19. The process of claim 1 in which the weight ratio of the liquid hydrocarbon solvent to solid carbonaceous material in the slurry is from about 1:1 to about 3:1.

20. The process of claim 1 in which the weight ratio of the liquid hydrocarbon solvent to solid carbonaceous material in the slurry is from about 1.5:1 to about 2.5:1.

21. A process for the production of methane which comprises in combination the steps of:
 (a) reacting a hydrogen containing gas with a slurry of particulate solid carbonaceous material in a liquid hydrocarbon solvent predominantly comprising hydrocarbons boiling in the range of from about 300° to about 750° F. and generated from the liquefaction of the carbonaceous material in the presence of hydrogen in a liquefaction zone maintained at a temperature from about 700° to about 1000° F. and at a pressure up to about 2500 psi for a time sufficient to convert a substantial portion of the carbonaceous material to fluid hydrocarbons and a solid residue of liquefaction, the weight ratio of the liquid hydrocarbon solvent to the carbonaceous material in the slurry being from about 1:1 to about 3:1;
 (b) combining the effluent of fluid hydrocarbons and the solid residue of liquefaction from the liquefaction zone with a synthesis gas in a stripping zone and forming a liquid-solids fraction comprising liquid hydrocarbons having a boiling point above the boiling point of the liquid hydrocarbon solvent and the solid residue of liquiefaction and a vapor fraction comprising hydrocarbons, carbon monoxide, carbon dioxide and hydrogen;
 (c) combining, in a gasification zone, the liquid-solids fraction from the stripping zone with oxygen and a source of combined oxygen in an amount sufficient to gasify substantially all of the carbon contained in the liquid-solids fraction to generate a synthesis gas comprising hydrogen and the oxides of carbon;
 (d) passing at least about 60% of the synthesis gas to the stripping zone to form the vapor fraction;
 (e) separating the vapor fraction into the liquid hydrocarbon solvent fraction, a light liquid hydrocarbon fraction and a residual vapor fraction comprising hydrocarbons containing up to about 5 carbon atoms, carbon dioxide, carbon monoxide and hydrogen;
 (f) returning at least a portion of the liquid hydrocarbon solvent fraction to the liquefaction zone;
 (g) converting the balance of the synthesis gas from the gasification zone into a hydrogen rich gas stream;
 (h) passing a portion of the hydrogen rich gas stream as at least part of the hydrogen containing gas to the liquefaction zone;
 (i) methanating at least a portion of the residual vapor fraction in the presence of steam and a high temperature methane forming alumina based catalyst containing from about 5 to about 50% by weight of at least one metal of the third period of Group VIII of the Periodic Table on a temperature stable alumina support in a first methanation zone having an inlet temperature of at least about 800° F. and exit temperature up to about 1500° F.;
 (j) combining, with steam, the effluent of the methanation zone, the balance of the residual vapor fraction and the light liquid hydrocarbon in a catalytic reforming stage where, at a temperature from about 1200° to about 1500° F. maintained by effluent of the methanation stage, hydrocarbons are reformed to yield an effluent gas stream comprising steam, hydrogen, carbon monoxide, carbon dioxide, and methane; and
 (k) passing the effluent gas stream from the reforming stage to at least one additional methanation stage where the hydrogen and carbon monoxide react to form additional methane.

22. The process of claim 21 in which the effluent of the reforming stage, prior to passage to an additional methanation stage is:
  (a) contacted in a hydrolysis zone with a catalyst to convert at least a portion of residual bound sulfur contained in the effluent of the reforming stage to hydrogen sulfide; and
  (b) treating the product of the hydrolysis zone to separate at least the formed hydrogen sulfide.

23. The process of claim 21 in which the liquid hydrocarbon solvent predominantly comprises hydrocarbons boiling in the range from about 500° to about 750° F.

24. The process of claim 21 in which liquefaction occurs at a temperature from about 800° to about 900° F.

25. The process of claim 21 in which from about 80 to about 90% of the synthesis gas is passed to the stripping zone.

26. The process of claim 21 in which the effluent gas from the reforming stage is at least passed through a plurality of methanation stages in series with cooling between each stage, each stage containing a high temperature methane forming alumina based catalyst containing from about 5 to about 50% of at least one metal of the third period of Group VII of the Periodic Table in a temperature of at least about 700° F. and an outlet temperature up to about 1500° F.

27. The process of claim 22 in which the effluent gas following treatment for hydrogen sulfide removal is at least passed through a plurality of methanation stages in series with cooling between each stage, each stage containing a high temperature methane forming alumina based catalyst containing from about 5 to about 50% of at least one metal of the third period of Group VIII of the Periodic Table in a temperature stable alumina support, each methanation stage having an inlet temperature of at least about 700° F. and an outlet temperature up to about 1500° F.

28. The process of claim 22 in which the weight ratio of the liquid hydrocarbon solvent to solid carbonaceous material in the slurry is from about 1.5:1 to about 2.5:1.

29. A process as claimed in claim 21 in which the alumina support is a temperature stabilized ceramic alumina heat treated to a temperature greater than the highest temperature in the methanation zone prior to the addition of the metal thereto.

30. A process as claimed in claim 21 in which the alumina support has a surface area of at least 30 m²/g and selected from the group consisting of gamma alumina, delta alumina, theta alumina, and mixtures thereof.

31. A process as claimed in claim 29 in which the support is modified with a potassium compound selected from the group consistng of potassium oxide, potassium carbonate, and mixtures thereof.

32. A process as claimed in claim 30 in which the alumina is modified with rare earth oxides.

33. A process as claimed in claim 30 in which the support is modified with a potassium compound selected from the group consisting of potassium oxide, potassium carbonate, and mixtures thereof.

34. A process for the production of methane which comprises in combination the steps of:
  (a) reacting a slurry of particulate coal in a liquid hydrocarbon solvent comprising hydrocarbons boiling up to about 750° F. and generated from the liquefaction of coal in the presence of hydrogen with a hydrogen containing gas in a liquefaction zone maintained at a temperature from about 700° to about 1000° F. and at a pressure up to about 2500 psi for a time sufficient to convert a substantial portion of coal to fluid hydrocarbons and a solid residue of liquefaction;
  (b) combining the effluent, fluid hydrocarbons and the solid residue of liquefaction from the liquefaction zone with a synthesis gas in a stripping zone and forming a liquid-solids fraction comprising liquid hydrocarbons boiling above the boiling point of the liquid hydrocarbon solvent and the solid residue of liquefaction and a vapor fraction comprising hydrocarbons, carbon monoxide, carbon dioxide, hydrogen sulfide and hydrogen;
  (c) combining, in a gasification zone, the liquid-solids fraction from the stripping zone with oxygen and a source of combined oxygen in an amount sufficient to gasify substantially all of the carbon contained in the liquid-solids fraction to generate a synthesis gas comprising hydrogen and the oxides of carbon;
  (d) passing a major portion of the synthesis gas to the stripping zone to form the vapor fraction;
  (e) separating the vapor fraction by cooling and condensation into a liquid hydrocarbon solvent fraction, a light liquid hydrocarbon fraction and a residual vapor frction comprising hydrocarbons containing up to about 5 carbon atoms, carbon dioxide, carbon monoxide and hydrogen;
  (f) returning at least a portion of the liquid hydrocarbon solvent fraction to the liquefaction zone;
  (g) converting a minor portion of the synthesis gas from the gasification zone into a hydrogen rich gas stream;
  (h) passing at least a portion of the hydrogen rich gas as at least part of the hydrogen containing gas to the liquefaction zone;
  (i) methanating a portion of the residual vapor fraction in the presence of steam and a high temperature methane forming alumina based catalyst containing from about 5 to about 50% by weight of at least one metal of the third period of Group VIII of the Periodic Table on a temperature stable alumina support in a first methanation zone having an inlet temperature of at least about 800° F. and exit temperature up to about 1500° F.;
  (j) combining, with steam, the effluent of the methanation zone, the balance of the residual vapor fraction and the light liquid hydrocarbon in a catalytic reforming stage where, at a temperature from about 1200° to about 1500° F. maintained by the effluent of the methanation stage, hydrocarbons are reformed to yield an effluent gas stream comprising steam, hydrogen, carbon monoxide, carbon dioxide and methane; and
  (k) passing the effluent gas stream from the reforming stage to at least one additional methanation stage where the hydrogen and carbon monoxide react to form additional methane.

35. The process of claim 34 in which the effluent of the reforming stage, prior to passage to an additional methanation stage, is:
  (a) contacted in a hydrolysis zone with a catalyst to convert at least a portion of residual bound sulfur contained in the effluent of the reforming stage to hydrogen sulfide, and (b) treating the product of the hydrolysis zone to separate at least formed hydrogen sulfide.

36. In a process for the recovery of hydrocarbon values from solid carbonaceous materials where there is formed a reformable liquid hydrocarbon and a vapor stream comprising hydrocarbons, carbon monoxide, carbon dioxide and hydrogen, an improvement for the production of methane from the reformable liquid hydrocarbon and the vapor stream which comprises:
(a) methanating a portion of vapor stream in the presence of steam and a high temperature methane forming alumina based catalyst containing from about 5 to about 50% by weight of at least one metal of the third period of Group VIII of the Periodic Table on a temperature stable alumina support in a first methanation zone having an inlet temperature of at least about 800° F., and an exit temperature up to about 1500° F.;
(b) combining, with steam, the effluent of the methanation zone, the balance of the vapor stream and the liquid hydrocarbon in a catalytic reforming stage where, at a temperature from about 1200° to about 1500° F. maintained by the effluent of the methanation stage, hydrocarbons are reformed to yield an effluent gas stream comprising steam, hydrogen, carbon monoxide, carbon dioxide and methane; and
(c) passing the efflunet gas stream from the reforming stage to at least one additional methanation stage where the hydrogen and carbon monoxide react to form additional methane in the presence of a high temperature methane forming alumina based catalyst containing from about 5 to about 50% by weight of at least one metal from the third period of Group VIII of the Periodic Table on a temperature stable alumina support, the inlet temperature to said methanation stage being at least about 700° F. and the exit temperature being up to about 1500° F.

37. The process of claim 36 in which the effluent of the reforming stage, prior to passage to an additional methanation stage is:
(a) contacted in a hydrolysis zone with a catalyst to convert at least a portion of residual bound sulfur contained in the effluent of the reforming stage to hydrogen sulfide, and
(b) treating the product of the hydrolysis zone to separate at least formed hydrogen sulfide.

38. A process as claimed in claim 37 in which the alumina support is a temperature stabilized ceramic alumina heat treated to a temperature greater than the highest temperature in the methanation zone prior to the addition of the metal thereto.

39. A process as claimed in claim 37 in which the alumina support has a surface area of at least 30 m$^2$/g and selected from the group consisting of gamma alumina, delta alumina, theta alumina, and mixtures thereof.

40. A process as claimed in claim 38 in which the support is modified with a potassium compound selected from the group consisting of potassium oxide, potassium carbonate, and mixtures thereof.

41. A process as claimed in claim 39 in which the alumina is modified with rare earth oxides.

42. A process as claimed in claim 39 in which the support is modified with a potassium compound selected from the group consisting of potassium oxide, potassium carbonate, and mixtures thereof.

* * * * *

UNITED STATES PATENT AND TRADEMARK OFFICE
CERTIFICATE OF CORRECTION

PATENT NO. : 4,115,075
DATED : September 19, 1978
INVENTOR(S) : Gerald P. McNamee et al It is certified that error appears in the above-identified patent and that said Letters Patent are hereby corrected as shown below:

Column 12, line 24, claim 21, "liquiefaction" should read -- liquefaction --.
Column 13, line 27, claim 26, "Group VII" should read -- Group VIII --.
Column 14, line 29, claim 34, "frction" should read -- fraction --; line 68, claim 35, "sulfide," should read -- sulfide; --.
Column 15, line 28, claim 36, "efflunet" should read -- effluent --.
Column 16, line 11, claim 37, "sulfide," should read -- sulfide; --.

Signed and Sealed this

Sixteenth Day of January 1979

[SEAL]

Attest:

RUTH C. MASON
*Attesting Officer*

DONALD W. BANNER
*Commissioner of Patents and Trademarks*